(12) United States Patent
Hamasaki et al.

(10) Patent No.: US 10,802,017 B2
(45) Date of Patent: Oct. 13, 2020

(54) BIOANALYSIS DEVICE AND BIOMOLECULE ANALYZER

(71) Applicant: HITACHI HIGH-TECHNOLOGIES CORPORATION, Tokyo (JP)

(72) Inventors: Koshin Hamasaki, Tokyo (JP); Toshiro Saito, Tokyo (JP)

(73) Assignee: HITACHI HIGH-TECH CORPORATION, Tokyo (JP)

( * ) Notice: Subject to any disclaimer, the term of this patent is extended or adjusted under 35 U.S.C. 154(b) by 0 days.

(21) Appl. No.: 14/768,771

(22) PCT Filed: Feb. 3, 2014

(86) PCT No.: PCT/JP2014/052376
§ 371 (c)(1),
(2) Date: Aug. 19, 2015

(87) PCT Pub. No.: WO2014/129292
PCT Pub. Date: Aug. 28, 2014

(65) Prior Publication Data
US 2016/0003814 A1 Jan. 7, 2016

(30) Foreign Application Priority Data
Feb. 22, 2013 (JP) ................. 2013-032718

(51) Int. Cl.
*G01N 21/64* (2006.01)
*G01N 33/543* (2006.01)
(Continued)

(52) U.S. Cl.
CPC .... *G01N 33/54333* (2013.01); *B01L 3/50273* (2013.01); *G01N 21/6428* (2013.01);
(Continued)

(58) Field of Classification Search
None
See application file for complete search history.

(56) References Cited

U.S. PATENT DOCUMENTS 4,849,340 A 7/1989 Oberhardt
6,294,342 B1 * 9/2001 Rohr ................ G01N 33/54333
324/200

(Continued)

FOREIGN PATENT DOCUMENTS

JP 1-502797 A 9/1989
JP 10-90278 A 4/1998
(Continued)

OTHER PUBLICATIONS

International Search Report received in corresponding International Application No. PCT/JP2014/052376.
(Continued)

*Primary Examiner* — Neil N Turk
(74) *Attorney, Agent, or Firm* — Mattingly & Malur, PC

(57) ABSTRACT

Paramagnetic fine particles of 1 micron or less used under a strong magnetic field were shown to form beads-like aggregates along the magnetic flux, and become irregularly shaped as such a mass of particles combines with a flat particle layer. This phenomenon becomes a factor that degrades the quality of quantification in bioanalysis. By confining a solution of microscopic magnetic fine particles between flat substrates of high wettability as thin a vertical thickness as possible and attracting the magnetic fine particles under a magnetic field applied from the side of one of the flat substrates, the magnetic fine particles can be evenly immobilized in the form of a film on the substrate surface in a dispersion state, and the quality of the biomolecule quantification can be improved.

12 Claims, 8 Drawing Sheets

(51) Int. Cl.
    *B01L 3/00* (2006.01)
    *G01N 27/74* (2006.01)

(52) U.S. Cl.
    CPC ..... *G01N 21/6486* (2013.01); *G01N 33/5434* (2013.01); *G01N 33/54326* (2013.01); *G01N 33/54346* (2013.01); *G01N 27/745* (2013.01); *G01N 2021/6439* (2013.01)

(56) References Cited

U.S. PATENT DOCUMENTS

| | | | |
|---|---|---|---|
| 2009/0321662 A1* | 12/2009 | Ohtsuka | G01N 21/05 250/459.1 |
| 2010/0120630 A1* | 5/2010 | Huang | B01J 19/0046 506/13 |
| 2011/0008776 A1 | 1/2011 | Warthoe et al. | |
| 2011/0065209 A1* | 3/2011 | Heil | C01N 33/54326 436/501 |
| 2012/0202194 A1 | 8/2012 | Evers et al. | |

FOREIGN PATENT DOCUMENTS

| | | | |
|---|---|---|---|
| JP | 2006-226940 A | 8/2006 | |
| JP | 2011-504592 A | 2/2011 | |
| JP | 2013-506125 A | 2/2013 | |

OTHER PUBLICATIONS

Rissin, D. M. et al., "Single-Molecule Enzyme-Linked Immunosorbent Assay Detects Serum Proteins at Subfemtomolar Concentrations", National Institute of Health Public Access, Nat Biotechnol, Jun. 2010, pp. 595-599.

\* cited by examiner

[FIG. 1]
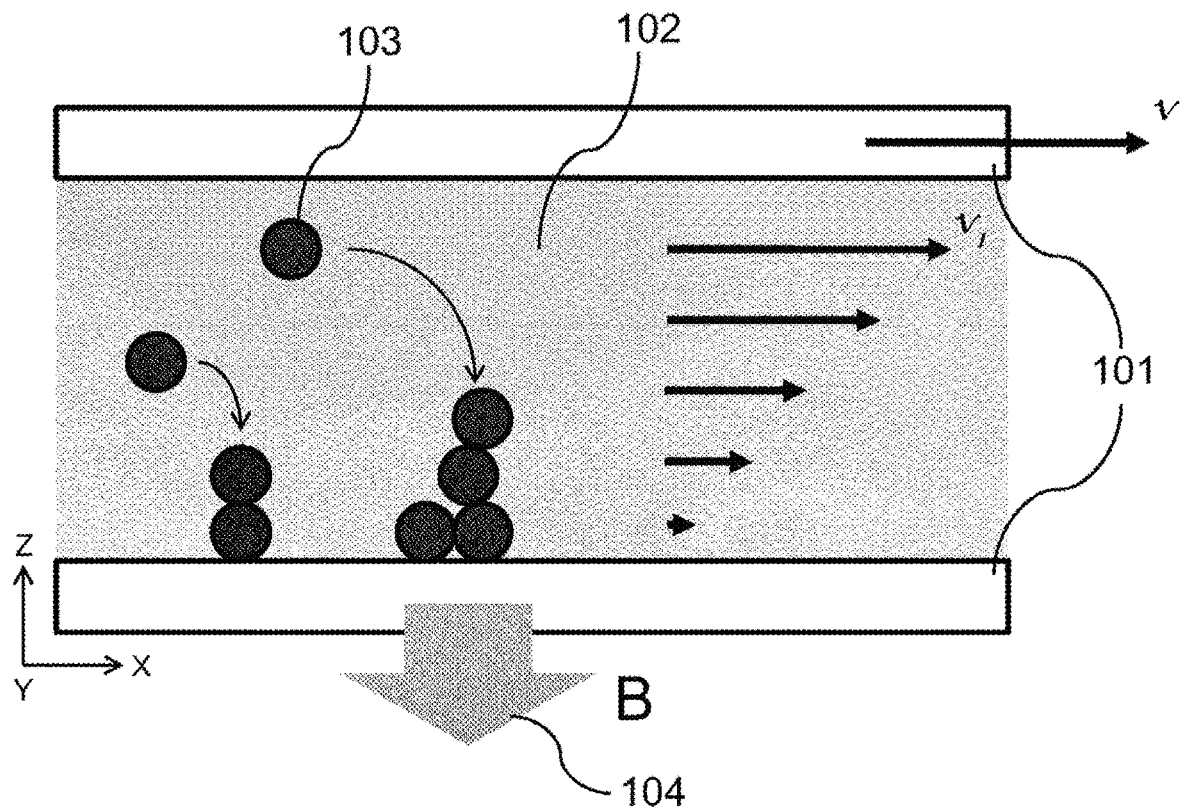
[FIG. 2]
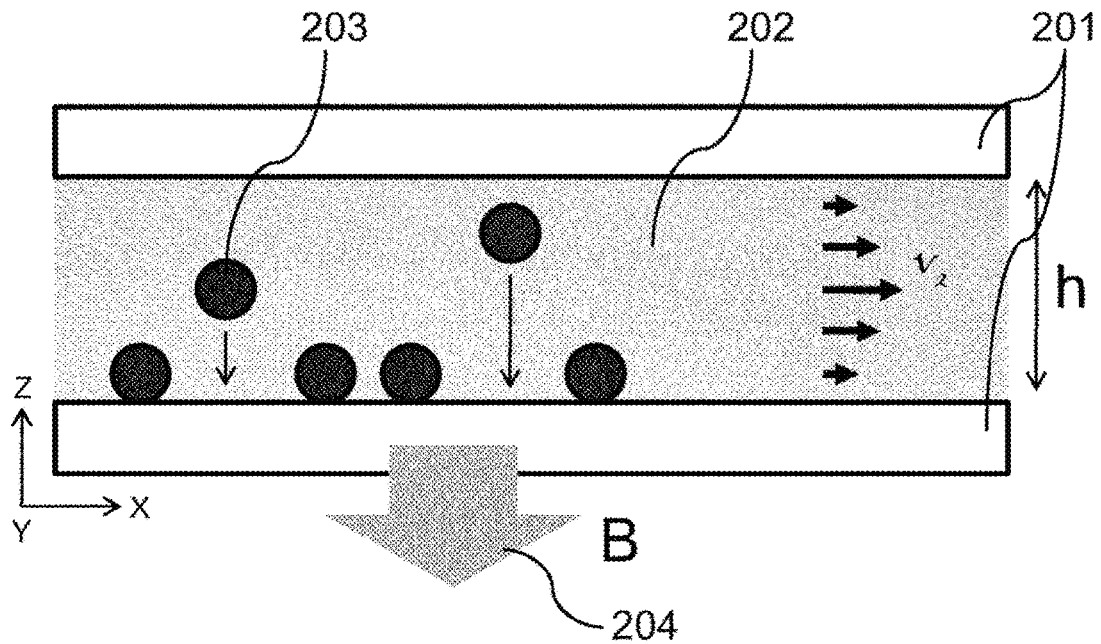

[FIG. 3]
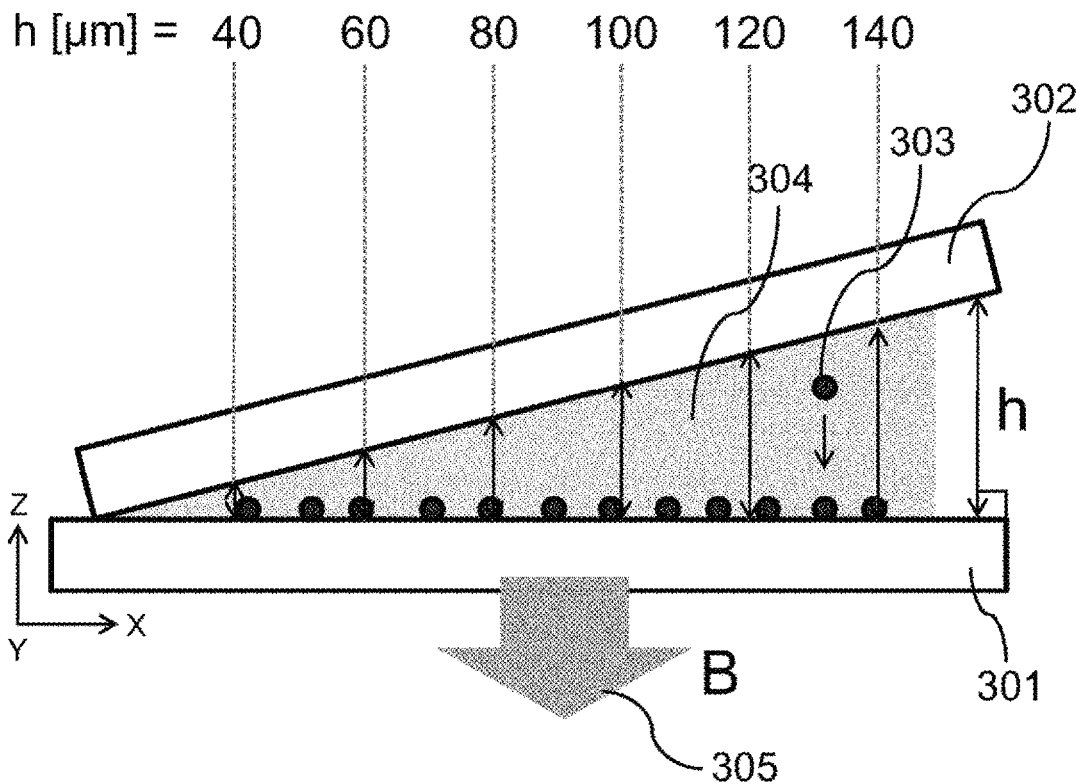
[FIG. 4]
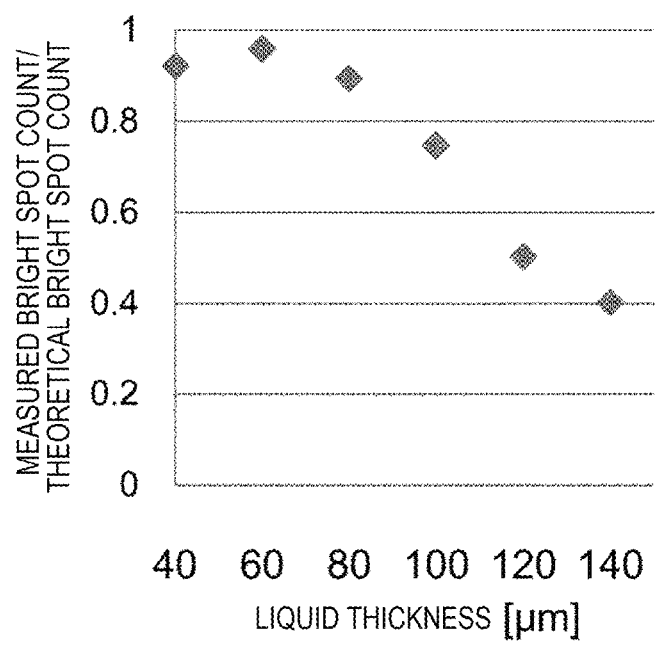

[FIG. 5]
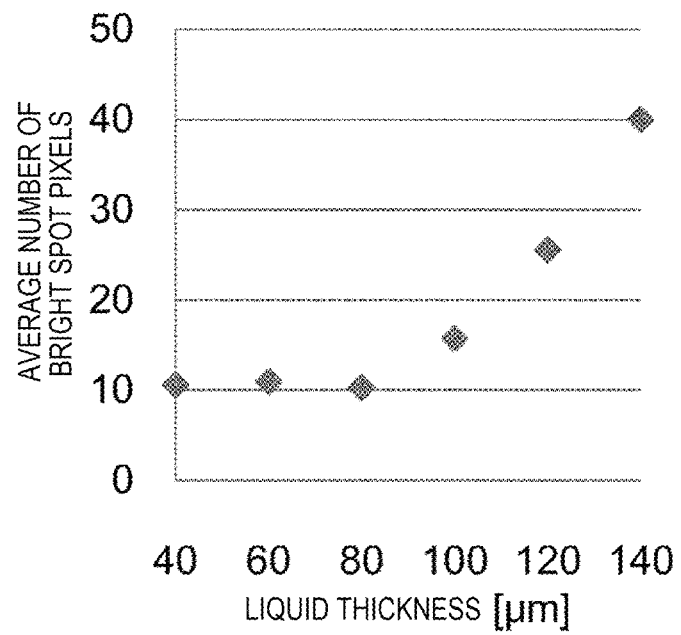
[FIG. 6]
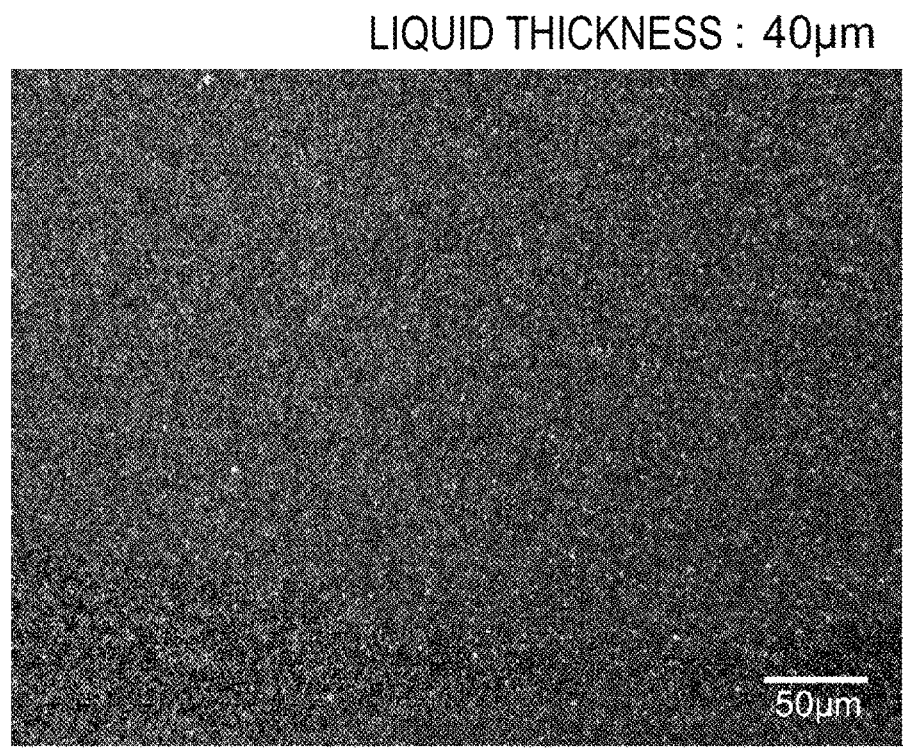

[FIG. 7]
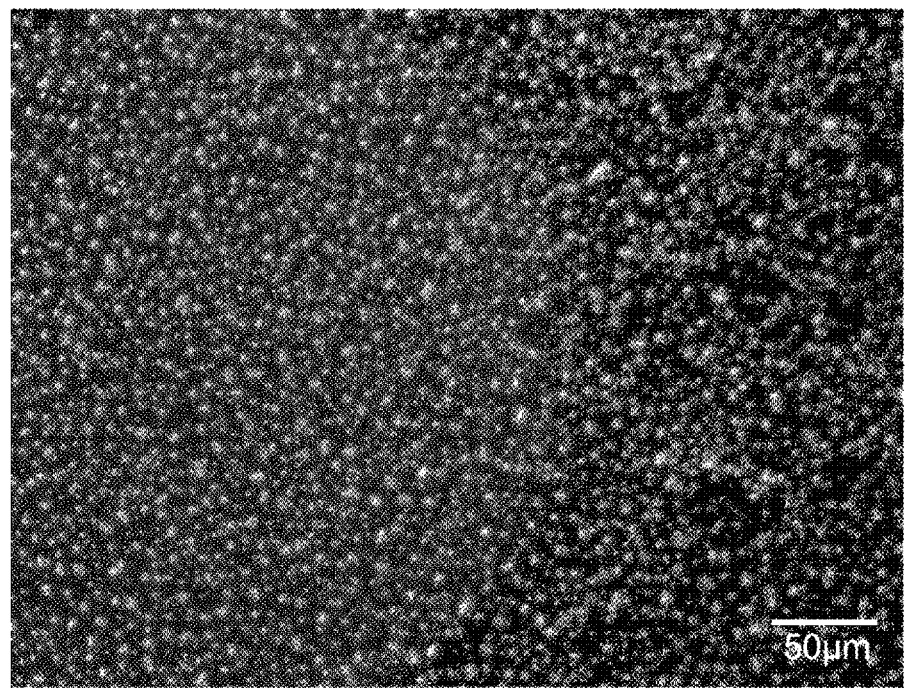

[FIG. 8]
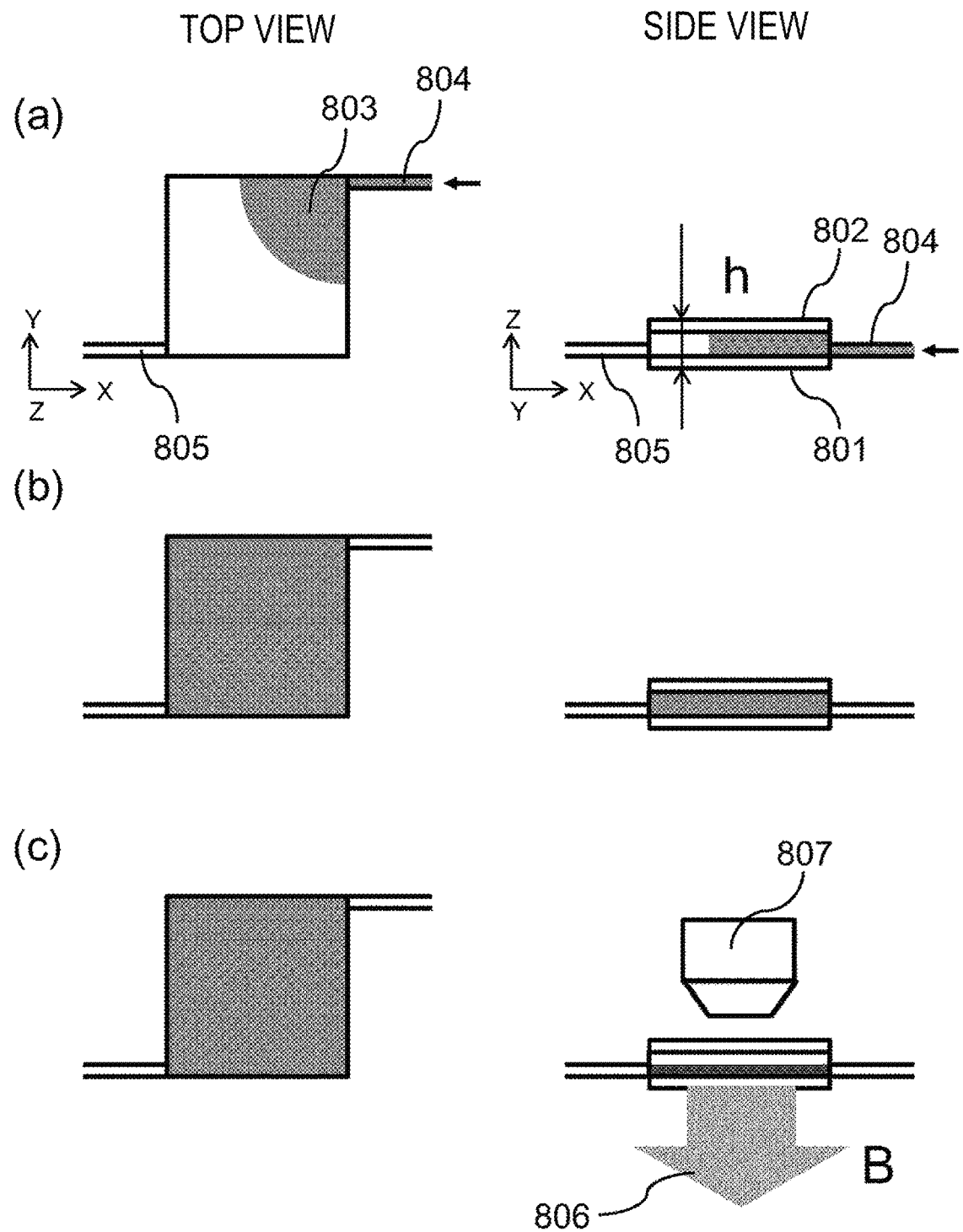

[FIG. 9]
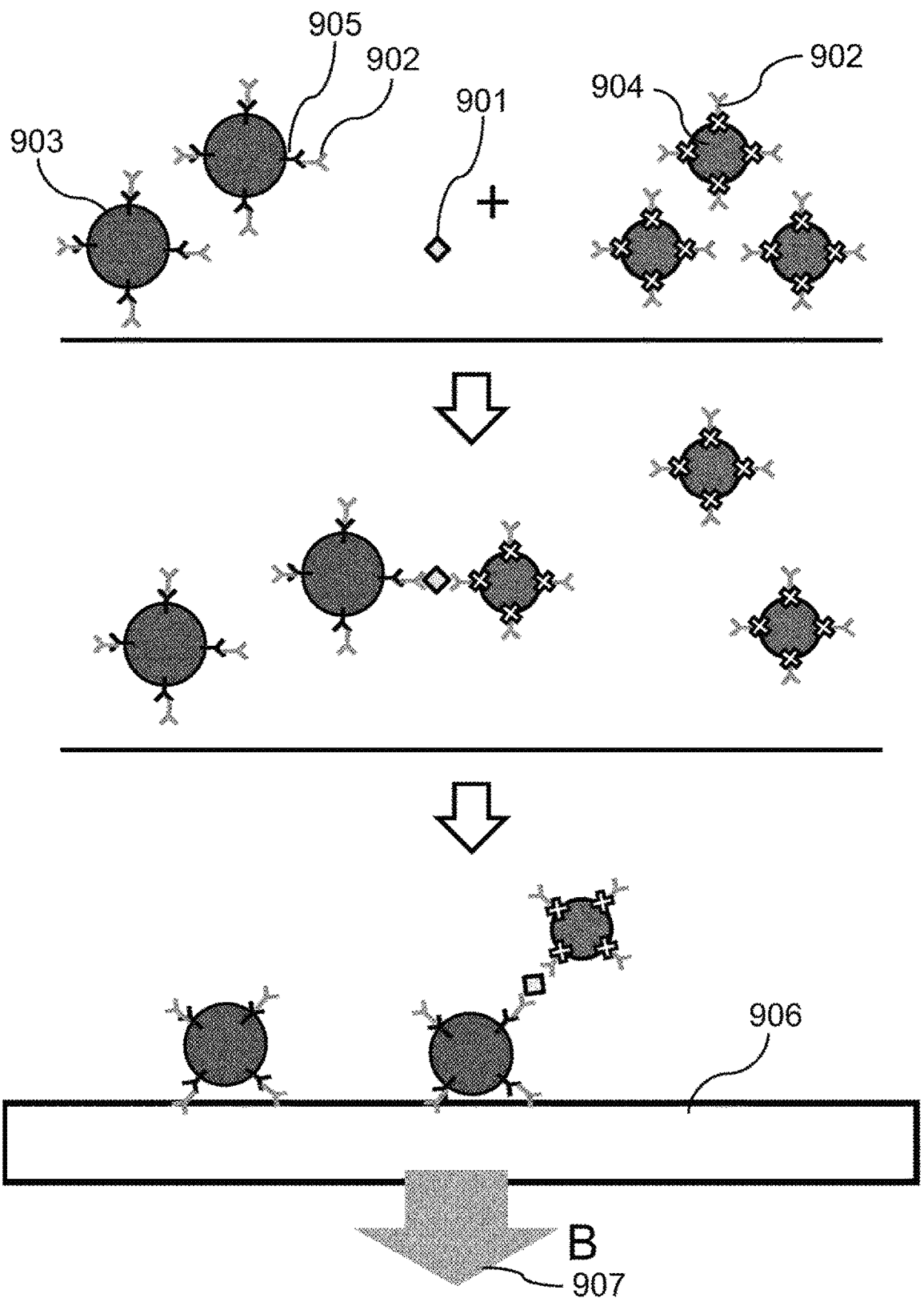

[FIG. 10]
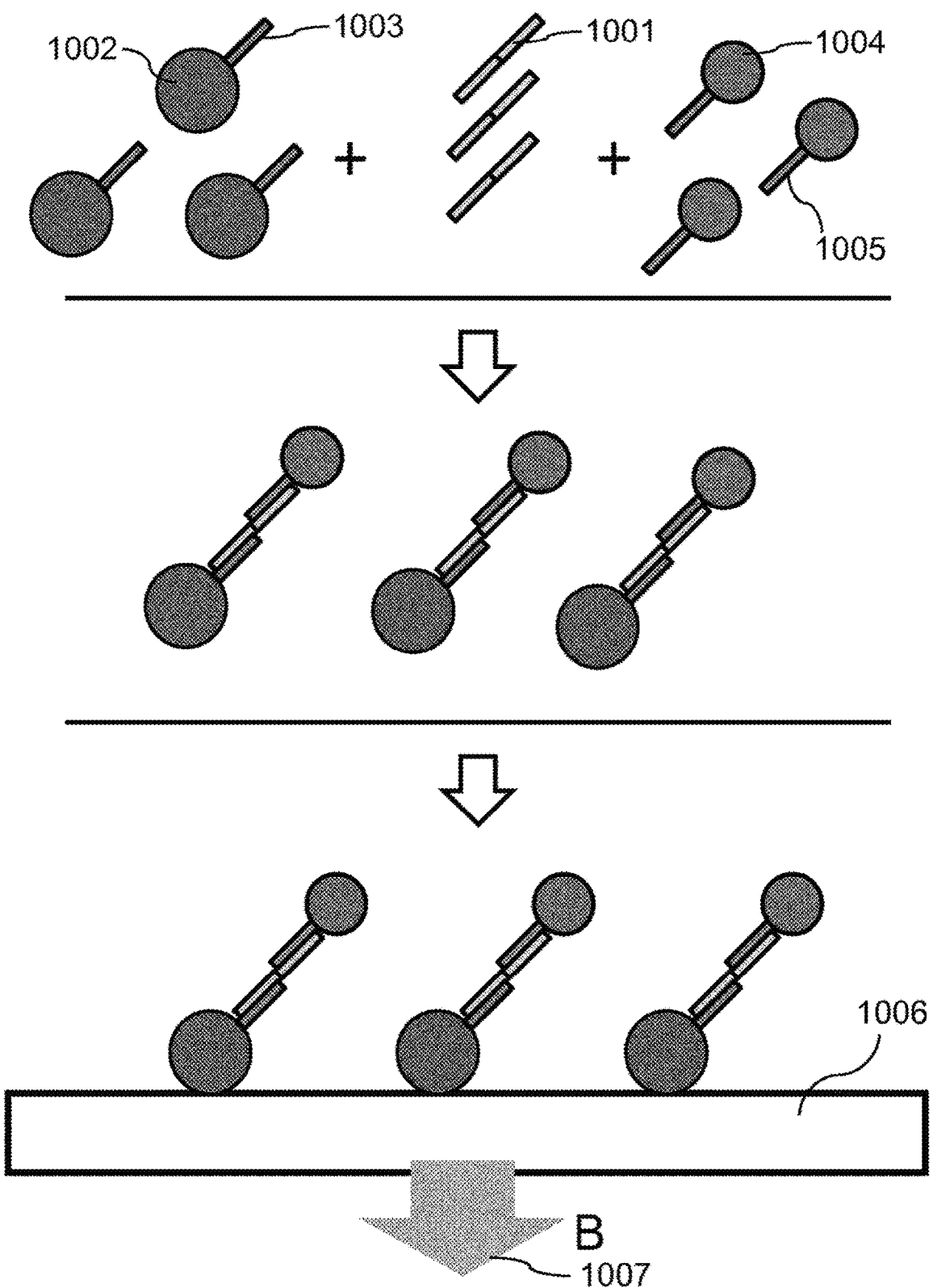

[FIG. 11]
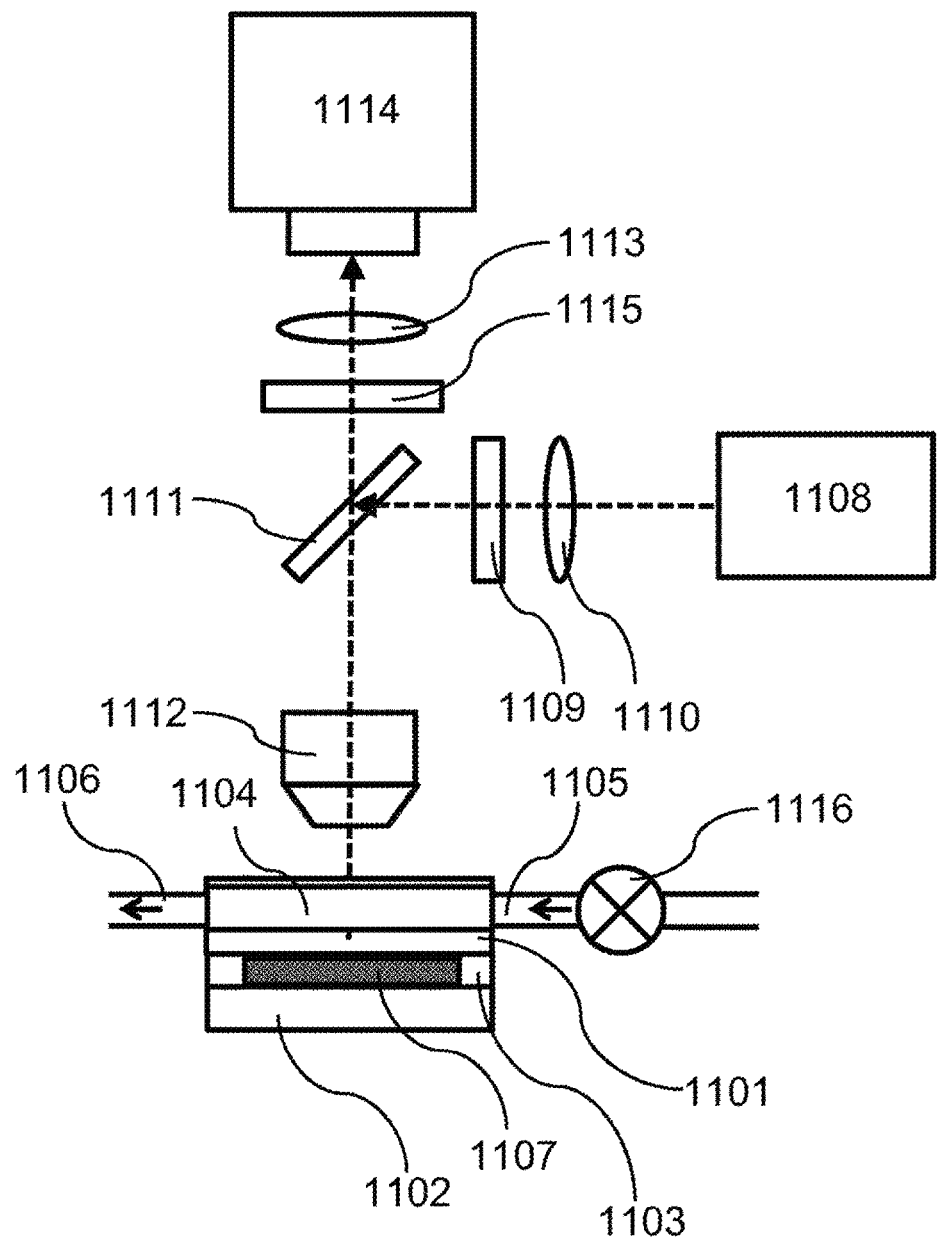

BIOANALYSIS DEVICE AND BIOMOLECULE ANALYZER

TECHNICAL FIELD

The present invention relates to a biomolecule analysis device, and to a biomolecule analyzer using same.

BACKGROUND ART

In the field of cancer diagnosis, there have been studies and actual applications of various cancer markers for finding early signs of cancer symptoms. Cancer markers are secretory biogenic factors of cancer-cell origin, and increase with cancer progression before they appear in blood or urine. Known examples include proteins such as hormones and cytokines, and nucleic acids such as microRNAs. These cancer markers occur in very small concentrations in early stages of cancer, and cannot be easily detected. Detection of cancer markers with inherently low expression levels is also difficult. Immunoassays using antibodies have become a mainstream method of high-sensitive cancer marker detection. Techniques such as ELISA and nanoparticle assay are known examples of such a method. Recent years have seen more sensitive immunoassays, such as the development of a digital ELISA that enables detection of single molecules (Non Patent Literature 1). In the detection of a cancer marker in blood, the amount of blood that can be collected from patients is limited, and trace amounts of cancer marker in blood need to be captured for detection in as many numbers as possible. Taking detection from 50 μl of blood plasma as an example, cancer markers are contained in a concentration range of $10^{-16}$ to $10^{-12}$ M in early stages of cancer, and the detection requires the sensitivity to quantify about 3000 target molecules contained in 50 μl of a sample. There accordingly is a need for a ultrasensitive detector that enables detection of such low concentrations of cancer markers.

CITATION LIST

Non Patent Literature

Non Patent Literature 1: Rissin D M et al, Nature Biotechnology, June 28(6); p. 595-599 (2010)

SUMMARY OF INVENTION

Technical Problem

The present invention relates to a method for quantifying trace amounts of biomolecules, to a structure of a quantification device, and to an analyzer configuration. Efficient capturing of trace amounts of biomolecules suspended in a solution typically requires increasing the frequency by which the target biomolecules collide with the molecules used to capture the target. Out of this demand, the present inventors have devised a method that makes use of microscopic magnetic fine particles of sizes no greater than 1 micron as the capture molecules. With the microscopic magnetic fine particles, the surface area per number of particles can be increased, and the molecular mobility can be improved for more efficient reaction with the target biomolecules. For the detection of biomolecules with fluorescent dye labels, observation is possible without interfering with the excitation and emission of the fluorescent dye when the sizes of the magnetic fine particles are about the same or smaller than the excitation wavelength and the emission wavelength. Fluorescence bright spots can thus still be obtained without degrading the quality of quantification even when all magnetic fine particles, including the particles that have captured the target biomolecules and the particles that did not capture the target biomolecules, are densely immobilized on a flat surface. It would thus be possible to quantify trace amounts of biomolecules by counting the number of biomolecules after all the magnetic fine particles that have captured the biomolecules are spread over a substrate of a certain area.

As described above, the method enables improving the capture efficiency, and increasing the density of immobilizable fine particles in a certain area by making the magnetic fine particles smaller. This is advantageous in terms of the sensitivity and speed of detection. However, smaller magnetic fine particles have low magnetic susceptibility, and do not easily magnetize. Spreading small magnetic fine particles over a flat substrate thus requires a strong magnetic field and a long magnetization time. In the presence of such a strong magnetic field, the magnetic fine particles have been shown to form beads-like aggregates along the magnetic flux, and become irregularly shaped as such a mass of particles combines with a flat particle layer. This phenomenon is commonly seen particularly at high magnetic fine particle concentrations. Formation of a large particle mass increases the height beyond the focal depth of an objective lens, and some of the fluorescence bright spots become out of focus, and degrade the quality of quantification. It might be possible to add an autofocus function to pick up all such unfocused fluorescence bright spots. However, this complicates the analysis, and increases the imaging time, both of which are disadvantageous for high-speed detection. There accordingly is a need for a means to densely and evenly immobilize high concentrations of microscopic magnetic fine particles.

Solution to Problem

A method is used in which a solution containing microscopic magnetic fine particles is confined between flat substrates of high wettability in as thin a vertical thickness as possible, and a magnetic field is applied from the side of one of the flat substrates to attract the magnetic fine particles. Alternatively, a device is used in which magnetic fine particles are flowed into a gap of a certain thickness created between a pair of highly wettable flat substrates, and a magnetic field is applied from the side of one of the flat substrates to immobilize the magnetic fine particles on the substrate.

Advantageous Effects of Invention

By confining the solution between flat substrates of high wettability in as thin a vertical thickness as possible, the magnetic fine particles can be evenly immobilized in the form of a film on the substrate surface in a dispersion state. This makes it easier to place the focal point on the fluorescent dye on the substrate, and blocking of excitation light due to trapping of the fluorescent dye by the magnetic fine particles can be prevented.

BRIEF DESCRIPTION OF DRAWINGS

FIG. 1 is a diagram explaining the general principle according to Example of the invention.

FIG. 2 is a diagram explaining the structure and the principle of the device of Example of the invention.

FIG. 3 is a diagram explaining a method for examining the principle according to Example of the invention.

FIG. 4 is a graph explaining the result of principle examination according to Example of the invention.

FIG. 5 is a graph explaining the result of principle examination according to Example of the invention.

FIG. 6 is a diagram explaining the result of principle examination according to Example of the invention.

FIG. 7 is a diagram explaining the result of principle examination according to Example of the invention.

FIG. 8 is a diagram explaining the device structure of Example of the invention.

FIG. 9 is a diagram explaining an example of the antigen molecule capturing method and the fluorescence labeling method according to Example of the invention.

FIG. 10 is a diagram explaining an example of the nucleic acid molecule capturing method and the fluorescence labeling method according to Example of the invention.

FIG. 11 is a diagram explaining an example of the configuration of the biomolecule analyzer according to Example of the invention.

DESCRIPTION OF EMBODIMENTS

Disclosed in Examples are a method for capturing analyte biomolecules on magnetic fine particles, a device structure with a flat and smooth supporting substrate for two-dimensionally presenting the fine particles, and procedures by which the fine particles are introduced onto the supporting substrate, and immobilized and observed thereon. The supporting substrate is not limited, as long as it is made of a material with desirable magnetic permeability, or has a sufficient magnetically permeable thickness. Particularly preferred are, for example, quartz glass substrates, and silicon substrates. The cover substrate used to seal a solution on the supporting substrate may be made of material, for example, such as inorganic glass and optical polymer that allow the passage of visible light. The wettability of the supporting substrate and the cover substrate should be as high as possible. For example, washed glass is most readily available. Hydrophobic polymers such as PDMS (polydimethylsiloxane) also may be used after a surface hydrophilic treatment performed by introducing an $O_2$ plasma or carboxyl groups. The substrate wettability is sufficient when it has a contact angle of about 10 to 30° for distilled water. However, the contact angle is more preferably less than 10° for improved effectiveness.

A magnetic field generator for attracting magnetic fine particles to the supporting substrate is installed directly below the supporting substrate. Desirably, the magnetic field generator has a function to switch on and off a magnetic field, or switch magnetic field strengths. The magnetic field generator may use, for example, an electromagnet, a movable permanent magnet, a movable electromagnet, a permanent magnet with a movable magnetic field shield placed between the supporting substrate and the magnet, or an electromagnet. The magnet is selected according to its magnetic force as may be suited for the type of the magnetic fine particles used. A strong magnetic field is needed particularly for immobilization of magnetic fine particles with a particle size of 300 nm or less, and such particles need to be attracted with a surface magnetic flux density of 0.1 T or more for a several seconds. Note here that the required magnetic force varies with the particles size of the magnetic fine particles, the ferrite content, the solvent, and the surface modification on the magnetic fine particles.

In the following, the term "device" is used to refer to a structure that includes the cover substrate above the supporting substrate, and in which the magnetic field generator is provided on the side of the supporting substrate with a certain space created to seal a solution between the substrates. The device is used by being installed on a movable stage so as to enable a whole scan of a supporting substrate surface.

Observation is performed in the following sequence. First, a reaction liquid containing magnetic fine particles having captured the target biomolecules thereon is placed on the supporting substrate, and the magnetic field generator is turned on to generate a magnetic field. The magnetic field attracts and immobilizes all the magnetic fine particles inside the reaction liquid on the supporting substrate. The magnetic fine particles immobilized on the supporting substrate with the bound fluorescence-labeled biomolecules are exposed to excitation light for imaging. The observed bright spots are then counted to determine the target biomolecule concentration.

Disclosed in Examples are analysis of biomolecules that are antigenic proteins (hereinafter, "antigens"). Specifically, an immunological analysis method is disclosed in which an analyte antigen prepared is bound to magnetic fine particles that have been conjugated to an antibody against the antigen, and to a fluorescently labeled antibody, and the labeled fluorescent product is detected. The method for producing the capture magnetic fine particles, and the fluorescence labeling method will be described in detail in the Examples below.

Also disclosed in Examples are a device with which analyte biomolecules are two dimensionally spread and immobilized under a magnetic field, and a biomolecule analyzer that includes the device and means by which the fluorescence of the fluorescent product is measured.

These and other novel features and effects of the present invention are described below with reference to the accompanying drawings. For a more complete understanding of the present invention, the following describes specific embodiments of the invention in detail. The present invention, however, is not limited by the contents of the following descriptions.

Example 1

This Example describes the principle of the present invention, examines the principle. Suppose that a solution 102 is sealed between a pair of parallel flat substrates 101 as shown in FIG. 1. In this case, it is known that moving the upper flat substrate 101 with a certain velocity v in x direction moves the fluid along with it in the vicinity of the substrate surface with a flow rate v1 approximately equal to velocity v (v1≈v), whereas the flow rate of the solution 102 approaches 0 toward the surface of the lower, fixed flat substrate 101. This is due to the generated frictional force between the sealed solution 102 and the flat substrates 101, and the fluid movement becomes more affected as the wettability of the flat substrates 101 increases. Accordingly, when a solution 202 is interposed in as thin a vertical thickness h as possible between highly wettable flat substrates 201 as shown in FIG. 2, most of the solution 202 will be in the vicinity of the surfaces of the substrates 201, and the middle portion of the solution 202, where the flow rate is the highest, can have a reduced maximum flow rate v2. In this state, attracting the magnetic fine particles 203 dispersed in the solution to the surface of one of the substrates with a magnetic field 204 of a magnetic flux density B generates a flow by the movement of the magnetic fine particles 203. However, because the horizontal flow is restricted, the magnetic fine particles 203 move in vertical direction along the magnetic field 204. Here, the magnetic fine particles 203 can be evenly immobilized in the form of a film on the substrate surface in a dispersion state, and the fluorescent dye on the substrate can easily be focused. Blocking of excitation light due to trapping of the fluorescent dye by the magnetic fine particles 203 also can be prevented.

In order to confirm these effects, a device was produced in which one side of the cover glass 302 disposed on a glass slide 301 was lifted up in the manner depicted in FIG. 3. A solution 304 containing magnetic fine particles 303 is injected into the gap between the two glass plates, and observed from different x-coordinate positions. This enables observation in varying liquid thicknesses of from 0 to 150 μm with a single substrate. Because the cover glass 302 is tilted, the thickness that appears in one field (430 μm×330 μm) differs by about 3 μm on the left and right side of the field. Liquid thickness h was thus determined as the liquid thickness at the field center. The solution 304 containing 16 pM of paramagnetic fine particles 303 having diameters of 300 nm was injected into the gap between the two glass plates, and the shape of the magnetic fine particles 303 attracted to the lower glass slide 301 under magnetic field 305 was observed from the scattered light for h=40, 60, 80, 100, 120, and 140 μm. For each liquid thickness, the number of bright spots, and the average number of bright spot pixels (bright spot size) were acquired from the resultant image.

The measured bright spot count obtained from the image was divided by the theoretical bright spot count determined from a given number of magnetic fine particles 303, and plotted against liquid thickness, as shown in FIG. 4. FIG. 5 represents a graph of average number of bright spot pixels plotted against liquid thickness. The result confirmed that the bright spot counts of the magnetic fine particles 303 remained the same for h=40 to 80 μm. However, the measured bright spot count/theoretical bright spot count ratio of the particles decreased to 0.8 or less above h=80 μm. On the other hand, it was confirmed that the diameters of the magnetic fine particles 303 (average number of bright spot pixels) increased with decrease in number of bright spots. This indicates that the aggregation of the magnetic fine particles 303 had proceeded with increasing liquid thicknesses. Immobilization patterns were also different. In contrast to the fine, densely immobilized particles observed for h=40 μm as shown in FIG. 6, formation of large particles was observed, and the particles were sparsely immobilized for h=140 μm, as shown in FIG. 7. Further, the tips of the particles appeared out of focus, confirming formation of about 2 to 3 μm aggregates in z-axis direction. Such unfocused particles were absent in images taken for thicknesses h of 100 μm and less, confirming that the magnetic fine particles 303 were immobilized in the form of a dense thin layer.

Example 2

Referring to FIG. 8, the following describes an example of procedures of a biomolecule measurement performed with the device that has been adjusted to make the liquid thickness 100 μm or less from the result described in Example 1. A 26×76 mm glass slide (Matsunami Glass) of 1.2-mm thickness was used as a supporting substrate 801 to immobilize magnetic fine particles in the device. An 8 mm×8 mm cover glass (Matsunami Glass) of 0.15-mm thickness was used as a cover member 802. These were washed with buffered hydrofluoric acid ($HF:NH_4F=1:200$) for 1 minute, or with 1 N KOH for 60 minutes, and a contact angle of 10° or less was confirmed with distilled water. A 0.05-mm thick polyimide tape (Chukoh Chemical Industries) that had been cut into a 1 mm width was then attached to the supporting substrate 801 to provide a square frame of a size that matched the cover member 802, and the cover member 802 was disposed thereon. As a result, a chamber measuring 7 mm×7 mm in size and 50 μm in height, having upper and lower glass plates was produced. Here, it is preferable to provide a solution inlet and an air outlet, rather than completely sealing the chamber. In this way, a solution 803 containing magnetic fine particles will be drawn into the chamber, and evenly spread therein by capillary action simply by being dropped in the vicinity of the inlet, as shown in FIG. 8, (a) and (b). This eliminates the need to pass the solution under high applied pressure, or to tightly seal the chamber. It is, however, desirable to insert a flow tube 804 having a hydrophobic surface, such as a silicon tube and a siliconized tip, into the inlet portion, and add the solution 803 through the flow tube 804 to prevent the solution 803 from leaking out of the chamber at the inlet portion. Similarly, it is desirable to dispose a hydrophobic discharge tube 805 to eject only the air at the outlet. In this Example, a silicon tube having an outer diameter of 1.0 mm and an inner diameter of 0.5 mm was used. The solution amount is adjusted according to the chamber volume. For example, in this Example, the solution was used in an amount of about 3 μl to apply the solution to the whole surfaces of the chamber. For example, 300-nm magnetic fine particles will have a density of $1.1\times10^7/mm^2$ when these are laid in a square-grid single layer over the supporting substrate 801. A single layer of magnetic fine particles can thus be obtained by introducing 3 μl of a 300 pM magnetic fine particle solution 803 into the chamber. When introducing the solution 803, the magnetic field 806 on the device needs to be turned off until the magnetic fine particles become evenly dispersed inside the chamber. The magnetic field 806 may be created by using a permanent magnet or an electromagnet. However, a method that installs and uninstalls a permanent magnet is least expensive and easiest. An electromagnet is convenient to use for switching on and off the magnetic field 806, but it makes the structure relatively large. In this Example, a permanent magnet was used to immobilize magnetic fine particles. A neodymium magnet (ø20 mm×10 mm) with a magnetic flux density of 0.5 tesla (T) was used as the permanent magnet. A holder for fixing the neodymium magnet was disposed immediately below the chamber, and the magnet was manually loaded and unloaded to switch on and off the magnetic field 806.

A method for preparing a sample is described below with reference to FIG. 9. When the biomolecule of interest for detection is an antigen 901, the antigen 901 is first captured on magnetic fine particles 903 that have been conjugated with antibody 902, and labeled with a fluorescent dye 904 that has been conjugated with antibody 902. All reactions are performed under ordinary temperature with a reaction buffer (tris buffer of pH 8.0, 50 mM NaCl, 0.1% Tween 20). The reaction between the antibody 902-conjugated magnetic fine particles 903 and the antigen 901, and the reaction between the fluorescence-labeled antibody 902 and the antigen 901 may be performed in either order, and may be simultaneously performed. The antigen 901 may be any antigen, whereas an antibody with high specificity to the antigen 901 is preferably selected for the antibody 902. For example, PSA (prostate specific antigen), a tumor marker for prostate cancer, was selected as antigen 901 in this Example. PSA antibodies need to be provided as antibodies that bind to the magnetic fine particles, and antibodies that are labeled with the fluorescent dye. The antibody 902 may be polyclonal antibody or monoclonal antibody, and the same antibody 902 may be used in the case of polyclonal antibody. The antibody 902 is appropriately selected according to the type of antigen 901. Desirably, a monoclonal antibody is selected for the magnetic fine particles, and a polyclonal antibody is selected for the fluorescent dye, and the antigen 901 is first reacted with the magnetic fine particles 903 that have been conjugated with the monoclonal antibody, and then with the polyclonal antibody. This is because a reaction with the polyclonal antibody may block the binding site on the antigen when this reaction precedes the reaction with the monoclonal antibody. For binding of the antibody 902 to the magnetic fine particles, the magnetic fine particles are prepared as particles with a secondary antibody 905 that can bind the antibody 902 while maintaining the activity of the antibody 902. The magnetic fine particles 903 are readily available from commercial products. For example, anti-mouse IgG-decorated Adembeads (ø300 nm; Ademtech) may be used as paramagnetic fine particles 903. The PSA antibodies are mixed and incubated in at least about 10 times the magnetic fine particles decorated with the secondary antibody 905. After capturing the magnetic fine particles 903 in a magnetic field 907, the solution is removed, and the conjugates are suspended in a clean buffer. This procedure is repeated until the majority of the unreacted antibodies are removed. Magnetic fine particles decorated with streptavidin also may be used as the magnetic fine particles 903. For example, streptavidin-decorated Adembeads (ø100 nm, ø200 nm, ø300 nm) available from Ademtech may be used. In this case, the antibody 902 is biotinylated, and bound to the surfaces of the magnetic fine particles 903.

Various fluorescent dyes are commercially available. Well known examples include FITC, Alexa®, and CY5. In order to enable detection of at least a single molecule of antigen 901, it is desirable in this experiment to use a high-luminance fluorescent dye having a long quench time. Examples of such fluorescent dyes include a dendrimer-type fluorescent dye in which several hundred molecules of fluorescent dye are bound to a single branching carbon chain; fluorescence polystyrene beads; and quantum dots.

In this Example, fluorescence polystyrene beads are used as fluorescent dye 904, and fluorescence labeling of antibody 902 with this fluorescent dye is described. For example, the fluorescence polystyrene beads used herein may be one that is available from Invitrogen under the trade name FluoSphere F8771®. These beads are coated with streptavidin, and can bind biotinylated antibody 902. The antigen 901 is captured between the antibody 902-conjugated fluorescence polystyrene beads and the antibody 902-conjugated magnetic fine particles. For the reaction, the antibodies 902 and the magnetic fine particles are introduced into a reaction vessel, and thoroughly stirred therein. After collecting the magnetic fine particles 903 under magnetic field 907, the supernatant containing the unreacted antibodies 902 is removed, and the conjugates are suspended in a reaction buffer. Thereafter, a solution with the antigen 901 to be detected is added to the suspension, thoroughly mixed, and incubated for 1 hour. Here, the reaction between antigen 901 and antibody 902 can be accelerated by vertically rotating the reaction vessel, or by shaking and agitating the reaction vessel. The antibody 902-conjugated magnetic fine particles 903 are mixed in excess of the antigen 901. Specifically, the antibody 902-conjugated magnetic fine particles 903 are added in 100 to 10000 times the estimated amount of antigen 901. The fluorescent dye 904-conjugated antibodies 902 are then added to the reaction liquid, and incubated for several minutes. The fluorescent dye 904-conjugated antibodies 902 are also added in excess of the antigen 901, specifically in 100 to 10000 times, or even in greater amounts with respect to the antigen 901. The excess addition increases the frequency of collision with the antigen 901, and improves the capture rate and the fluorescence labeling rate of the antigen 901. After the reaction, the unreacted fluorescence-labeled antibodies are washed away. The reaction liquid is diluted with washing buffer used in about 5 times the amount of the reaction liquid, and the dilute reaction liquid in the micro tube is inserted into a magnetization magnet holder, and allowed to stand for 2 minutes. Upon checking that the magnetic fine particles have been collected on the wall surface, the supernatant is completely removed with care that the magnetic fine particles are not aspirated. Thereafter, the same amount of washing buffer is added, and the magnetic fine particles are suspended therein and magnetized. This procedure is repeated about 5 to 7 times to remove the unreacted antibodies 902 conjugated with the fluorescent dye 904. After the final removal of washing buffer, the liquid is concentrated to an amount to be introduced into the device, and the total amount is injected into the device. During the injection, the magnetic field 806 on the device is switched off to allow the liquid to evenly spread inside the device. The magnetic field 806 is switched on upon checking that all the liquid has entered the device. In the presence of the magnetic field 806, formation of film-like magnetic fine particles was confirmed. The preferred configuration of a bioanalyzer that includes the device and an incident-light microscope will be described in detail in Example 4 below. The device was placed on an automated stage, and exposed to excitation light through an objective lens 807 from above as shown in FIG. 8, (c). In about 500 fields of scanned image, fluorescence bright spots were observed with hardly any trapping loss by the magnetic fine particles 903.

Example 3

Referring to FIG. 10, this Example describes procedures in which the biomolecule of interest for detection is a nucleic acid fragment. First, a sample nucleic acid fragment 1001 as a detection target is captured on magnetic fine particles 1002, and labeled with a fluorescent dye 1004-conjugated nucleic acid fragment 1005 having a sequence 1003 complementary to the sample nucleic acid fragment 1001. This is a specific hybridization reaction, and was performed in a reaction buffer (PBS buffer of pH 7.4, 50 mM to 1 M NaCl, 0.1% Tween 20). The reaction between the nucleic acid-conjugated magnetic fine particles 1002 and the sample nucleic acid fragment 1001, and the reaction between the fluorescent dye 1004-conjugated nucleic acid fragment 1005 and the sample nucleic acid fragment 1001 may be performed in either order, and may be simultaneously performed. The nucleic acid fragment may be a single-strand DNA or RNA. The following specifically describes an example in which microRNA was used as analyte.

MicroRNA is a single-stranded nucleic acid fragment of about 20 mer. For detection, an adapter nucleic acid sequence 1003 is bound to the 3' end of the microRNA used as the sample nucleic acid fragment 1001. For example, a 20-mer poly-A sequence may be used. Thereafter, the complementary sequence fragment 1005 for the adapter is bound to the fluorescent dye 1004. The fluorescent dye 1004 with the complementary sequence fragment 1005 for the adapter was then mixed with the sample nucleic acid fragment 1001, and incubated at room temperature for about 1 hour. Separately, magnetic fine particles 1002 were prepared as particles with a complementary sequence fragment 1003 for the sample nucleic acid fragment 1001, and mixed with the sample nucleic acid fragment 1001 previously reacted with the fluorescent dye 1004. The mixture was then incubated at room temperature for about 1 hour in the same manner as above.

The method described in this Example uses streptavidin-decorated Adembeads (ø100 nm; Ademtech) as magnetic fine particles 1003, and quantum dots as fluorescent dye 1004. Quantum dots are semiconductor fine particles with diameters of several nanometers to several ten nanometers. Quantum dots have a longer lifetime, and are brighter than conventional fluorescent dyes, and different particle sizes fluoresce in different wavelengths. Various types of quantum dots are commercially available, and some are decorated with various functional groups. For example, Invitrogen Qdot 655 Streptavidin®, capable of binding any antibodies may be used as quantum dots, and may be bound to a biotinylated labeled nucleic acid fragment.

For example, the streptavidin-decorated Qdot® available from Invitrogen may be used. The binding between the quantum dots and the nucleic acid fragments may be achieved by incubating the mixture of these for at least 30 minutes. The unreacted nucleic acid fragments are removed by using a spin column with a cutoff of 50 kDa after the reaction.

The magnetic fine particles with the capture sequence fragment, the fluorescent dye-labeled nucleic acid fragment, and the microRNA adjusted to a concentration of 1 to 100 pM were mixed after being prepared in the manner described above, and the mixture was incubated for 6 hours after being thoroughly stirred. Here, the hybridization reaction can be accelerated by vertically rotating the reaction vessel, or by shaking and agitating the reaction vessel. The magnetic fine particles are mixed in excess of the target nucleic acid fragments. Specifically, the magnetic fine particles were added in 100 to 10000 times the estimated amount of the sample in terms of the number of molecules.

The reaction liquid prepared as above was placed on a supporting substrate 1006, and observed under the attractive force of a magnetic field 1007 as in Example 2. It was found that the total number of bright spots in each sample was proportional to the concentration of the reacted microRNA. Further, with the diameter ø of 100 nm, it was possible to immobilize the magnetic fine particles in a density as high as about 9 times that observed in Example 2 in which the same number of magnetic fine particles was used. Accordingly, the detection time improved by a factor of about 9.

Example 4

An example of the preferred configuration of the biomolecule analyzer is described in detail below with reference to FIG. 11. The biomolecule analyzer of this Example includes the device that attracts and retains magnetic fine particles on a supporting substrate 1101 under a magnetic field. The device is provided as an integral unit with means to illuminate the supporting substrate 1101 with light, means to supply an analyte biomolecule solution, means to measure fluorescence, and means to operate the supporting substrate.

Specifically, a light microscope with a movable stage 1102 was used. A magnet holder 1103 was placed on the movable stage 1102, and a device 1104 was fixed thereon. The device is joined to a flow tube 1105 and a discharge tube 1106 in advance. A silicon tube was used as the flow tube 1105. After introducing a biosample solution to the device 1104, a magnetic field generator 1107 was used to generate a magnetic field, and attract and immobilize the magnetic fine particles on the surface of the supporting substrate 1103. An excitation light source 1108 is appropriately selected according to the type of the fluorescent product used. For example, a mercury lamp was used as the light source 1108 when quantum dots were used as the fluorescent dye for fluorescence labeling. Use of 532 nm (a YAG laser) is also possible. The excitation filter 1109 and the excitation light from the excitation light source 1108 travel through a lens 1110, and are guided into an objective lens 1112 off a dichroic mirror 1111 to illuminate the supporting substrate 1101. The fluorescence that generates from the fluorescence-labeled molecules on the supporting substrate 1107 propagates in the same light path as the excitation light in the opposite direction, and collected through the objective lens 1112. The light then passes the dichroic mirror 1111, and forms an image on the light-sensitive surface of a two-dimensional CCD camera 1114 through an imaging lens 1113. The scattered rays of the excitation light are removed by an absorbing filter 1115. The observable bright spots need to be increased to improve the quality of quantification. This can be achieved by moving the movable stage 1103 at high speed, and scanning the whole surface of the supporting substrate 1101 in shorter time periods. It was possible to scan an area of 100 fields (16 mm$^2$) in about 3 minutes with the biomolecule analyzer built from the 20 times objective lens 1112, a flow pump 1116, the excitation light source 1108, the fluorescence detecting unit, the magnetic field generator 1107, and the movable stage 1103. This rate is equivalent of observing $1.8 \times 10^7$ magnetic fine particles in 3 minutes in a single layer of magnetic fine particles.

REFERENCE SIGNS LIST

101 Flat substrate
102 Solution
103 Magnetic fine particles
104 Magnetic field
201 Flat substrate
202 Solution
203 Magnetic fine particles
204 Magnetic field
301 Glass slide
302 Cover glass
303 Magnetic fine particles
304 Solution
801 Supporting substrate
802 Cover member
803 Solution
804 Flow tube
805 Discharge tube
806 Magnetic field
901 Antigen
902 Antibody
903 Magnetic fine particles
904 Fluorescent dye
905 Secondary antibody
906 Flat substrate
907 Magnetic field
1001 Sample nucleic acid fragment 1002 Magnetic fine particles
1003 Complementary sequence fragment for sample
1004 Fluorescent dye
1005 Complementary sequence fragment for adapter
1006 Supporting substrate
1007 Magnetic field
1101 Supporting substrate
1102 Movable stage
1103 Magnet holder
1104 Device
1105 Flow tube
1106 Discharge tube
1107 Magnetic field generator
1108 Excitation light source
1109 Excitation filter
1110 Lens
1111 Dichroic mirror
1112 Objective lens
1113 Imaging lens
1114 CCD camera
1115 Absorbing filter
1116 Flow pump

The invention claimed is:

1. A biomolecule analyzing device comprising:
a solution of magnetic fine particles, some of which have a target antigen molecule or target nucleic acid molecule captured thereon by an antibody and labelled with a fluorescent dye and some of which do not have the target antigen molecule or target nucleic acid molecule captured thereon, the magnetic fine particles having a particle size less than or equal to 300 nm;
a solution vessel having a highly wettable hydrophilic cover substrate opposite a highly wettable hydrophilic supporting substrate which confine the solution in the solution vessel, the solution vessel defining a chamber for the solution by providing the supporting substrate within the chamber having a shape and area corresponding to the shape and area of the cover substrate;
a magnetic field generator configured to generate a magnetic field with a surface magnetic flux density of at least 0.1 Tesla (T) and that is disposed below the supporting substrate, wherein the magnetic field generator is further configured to switch the magnetic field on and off, or switche strengths of the magnetic field including at least one strength of at least 0.1 T to immobilize the magnetic fine particles of the solution onto and directly contacting a surface of the supporting substrate;
an excitation light source to irradiate the fluorescent dye bound to the magnetic fine particles; and
a camera to acquire an image of bright spots from light emitted from the fluorescent dye bound to the magnetic fine particles,
wherein a width between the supporting and cover substrates is 50 μm or less, and
wherein a measured bright spot count of the bright spots obtained from the image is greater than 80% of a theoretical bright spot count.

2. The biomolecule analyzing device according to claim 1, wherein the supporting and cover substrates have a surface contact angle of 30° or less for distilled water.

3. The biomolecule analyzing device according to claim 1, further comprising:
a solution inlet coupled to the solution vessel and a first hydrophobic tube configured to prevent the solution from leaking out of the solution inlet and an air outlet coupled to a second hydrophobic discharge tube configured to eject only air from the air outlet,
wherein the solution is introduced into the solution vessel by capillary action created by the supporting and cover substrates.

4. The biomolecule analyzing device according to claim 1, wherein the magnetic field generator is one of an electromagnet, a movable permanent magnet, an electromagnet coupled to a movable magnetic field shield, and a permanent magnet coupled to a movable magnetic field shield.

5. The biomolecule analyzing device according to claim 1, further comprising:
inlet and outlet flow tubes having hydrophobic surfaces and which are joined to an inlet and an outlet, respectively, of the solution vessel.

6. The biomolecule analyzing device according to claim 1, wherein the solution includes the target antigen molecules captured on the magnetic fine particles through an antigen-antibody reaction.

7. The biomolecule analyzing device according to claim 1, wherein the solution includes the target nucleic acid molecules captured on the magnetic fine particles through hybridization.

8. The biomolecule analyzer according to claim 1, wherein the cover substrate is a glass or an optical polymer subjected to a hydrophilic treatment.

9. The biomolecule analyzer according to claim 1, further comprising:
an objective lens to guide the light from the light source to the solution vessel and to receive the light emitted from the fluorescent dye bound to the magnetic fine particles.

10. The biomolecule analyzer according to claim 1, wherein the magnetic fine particles have the particle size greater than or equal to 20 nm.

11. The biomolecule analyzer according to claim 1, wherein the width between the supporting and cover substrates is 40 μm or more and 50 μm or less.

12. The biomolecule analyzer according to claim 1, wherein the supporting substrate is formed from one of quartz glass and silicon.

* * * * *